(12) United States Patent
Tumlinson et al.

(10) Patent No.: US 8,998,411 B2
(45) Date of Patent: Apr. 7, 2015

(54) LIGHT FIELD CAMERA FOR FUNDUS PHOTOGRAPHY

(75) Inventors: Alexandre R. Tumlinson, San Leandro, CA (US); Matthew J. Everett, Livermore, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 279 days.

(21) Appl. No.: 13/542,516

(22) Filed: Jul. 5, 2012

(65) Prior Publication Data
US 2013/0010260 A1    Jan. 10, 2013

Related U.S. Application Data

(60) Provisional application No. 61/505,912, filed on Jul. 8, 2011.

(51) Int. Cl.
*A61B 3/14* (2006.01)
*A61B 3/15* (2006.01)
*H04N 5/225* (2006.01)

(52) U.S. Cl.
CPC . *A61B 3/158* (2013.01); *A61B 3/14* (2013.01); *A61B 3/152* (2013.01); *H04N 5/225* (2013.01)

(58) Field of Classification Search
CPC .......... G61B 3/10; G61B 3/112; G61B 3/117; G61B 3/14; G61B 3/145; G61B 3/15; G61B 3/152; G61B 3/154; G61B 3/158; A61B 3/10; A61B 3/112; A61B 3/117; A61B 3/14; A61B 3/145; A61B 3/15; A61B 3/152; A61B 3/154; A61B 3/158
USPC .................. 351/204, 205, 206, 210, 221, 246
See application file for complete search history.

(56) References Cited

U.S. PATENT DOCUMENTS

| | | | |
|---|---|---|---|
| 4,998,818 A | 3/1991 | Kugler et al. | |
| 5,177,511 A | 1/1993 | Feuerstein et al. | |
| 6,065,837 A | 5/2000 | Goldfain et al. | |
| 7,364,295 B2 | 4/2008 | Tawada | |
| 7,780,364 B2 | 8/2010 | Raskar et al. | |
| 7,936,392 B2 | 5/2011 | Ng et al. | |
| 8,243,157 B2 * | 8/2012 | Ng et al. | 348/222.1 |

(Continued)

FOREIGN PATENT DOCUMENTS

EP  1983318 A1  10/2008
WO  2010/045564 A2  4/2010

OTHER PUBLICATIONS

Canon Inc., "Canon Successfully Develops World's First Aps-H-Size Cmos Image Sensor to Realize Record-High Resolution of 120 Megapixels", News Releases, online available at <www.canon.com/news/2010/aug24e.html>, Aug. 24, 2010, 2 pages.

(Continued)

*Primary Examiner* — Huy K Mai
(74) *Attorney, Agent, or Firm* — Morrison & Foerster LLP

(57) ABSTRACT

Systems and methods for applying the concept of lightfield sensors to fundus photography are presented. In one embodiment, the ability to isolate specific regions of the collected lightfield are used to reduce the effects of glare in a fundus image. Additional embodiments in which aberrations can be characterized and removed, an image from a particular plane in the collected light field is used to aid in instrument alignment, and dynamic optimization of collection pupil diameter is accomplished are also presented.

25 Claims, 5 Drawing Sheets

(56) References Cited

U.S. PATENT DOCUMENTS

| | | |
|---|---|---|
| 8,471,897 B2 | 6/2013 | Rodriguez Ramos et al. |
| 2009/0273843 A1 | 11/2009 | Raskar et al. |
| 2013/0169934 A1 | 7/2013 | Verdooner |

OTHER PUBLICATIONS

DeHoog et al., "Fundus Camera Systems: A Comparative Analysis", Applied Optics, vol. 48, No. 2, Jan. 10, 2009, pp. 221-228.

Georgiev et al., "Focused Plenoptic Camera and Rendering", Journal of Electronic Imaging, vol. 19, No. 2, Apr.-Jun. 2010, pp. 021106-1-021106-11.

Lumsdaine et al., "The Focused Plenoptic Camera", ICCP, Apr. 2009, 8 pages.

Ng et al., "Light Field Photography with a Hand-held Plenoptic Camera", Stanford Tech Report, CTSR, 2005, pp. 1-11.

Ng, Ren, "Digital Light Field Photography", Submitted to the Department of Computer Science and the Committee on Graduate Studies of Stanford University, Jul. 2006, 203 pages.

Perwaβ et al., "The Next Generation of Photography : An Introduction to Light Field Photography", Raytrix GmbH, available online at <http://www.raytrix.de/index.php/Technology.html>, Jan. 2010, pp. 1-33.

Raskar et al., "Glare Aware Photography: 4D Ray Sampling for Reducing Glare Effects of Camera Lenses", Mistubishi Electric Research Laboratories, Aug. 2008, 12 pages.

Tokuda et al., "Holocamera for 3-D Micrography of the Alert Human Eye", Applied Optics, vol. 19, No. 13, Jul. 1, 1980, pp. 2219-2225.

International Search Report and Written Opinion received for PCT Patent Application No. PCT/EP2012/063192, mailed on Sep. 19, 2012, 12 pages.

\* cited by examiner

LIGHT FIELD CAMERA FOR FUNDUS PHOTOGRAPHY

PRIORITY

This application claims priority to U.S. Provisional Application Ser. No. 61/505,912 filed Jul. 8, 2011, the contents of which are hereby incorporated by reference.

TECHNICAL FIELD

One or more embodiments of the present invention relate to the field of fundus imaging. In particular, the invention described herein provides systems and methods for using light field imaging technology in fundus photography including but not limited to embodiments to reduce glare, assist in instrument alignment, correct aberrations, and create stereo images.

BACKGROUND

A traditional image is created when a sensor is placed in an optical system at a plane optically conjugate to an object which is to be imaged. This is the plane at which the best focus is achieved and therefore the best optical resolution of features in the object results. By design, rays emanating from a point within the object plane in multiple directions are captured by the optical system and those rays converge to approximately a single point in the conjugate image plane. The set of rays which are summed at any image point is generally constrained by physical apertures placed within the optical assembly. The traditional sensor records the summation of the intensity of light in the plane of the detector. The measurement contains the intensity distribution of light within the plane of the sensor but loses all information about the rays' direction before the summation. Therefore the process of recording a traditional image throws away a very large fraction of the information contained in the light absorbed.

As described by Ren Ng, the "light field" is a concept that includes both the position and direction of light propagating in space (see for example U.S. Pat. No. 7,936,392). The idea is familiar from the ray representation of light. We know that light energy is conserved as it passes along straight line paths through space. The light energy can be represented in a 4 dimensional space $L(u,v,s,t)$ with an intensity value at each of $(u,v)$ positions within a plane, and at angular rotations $(s,t)$ about each of those axes. The concept is used extensively in computer graphics simulations. With the information from a light field, the rays can be propagated to destinations in other planes. The process of computing the light intensity at another plane and presenting it as if it were imaged on a virtual film is also called reconstruction. The methods described by U.S. Pat. No. 7,936,392 B2, as well as the doctoral thesis by the same author (R. Ng, "Digital light field photography" 2006) are exemplary descriptions of lightfield sensor technology, the mathematics for propagation of the light fields, and the practice of image reconstruction techniques using light fields, both of which are hereby incorporated by reference A light field sensor for use in a digital focus camera is achieved by placing a sensor array 101 at or near the back focal plane of a lens array (lenticular array) 102 as illustrated in FIG. 1. This light field sensor is placed in a supporting assembly containing other optical components such as a main lens 103 to shape and constrain the light from the subject 104 to best fit the light field sensor geometry. In this way a ray is constrained in position by the individual lens in the array (lenslet) through which it passed, and in angle by the specific sensor pixel it is incident upon behind the lenticular array. Light field sensors may be created by other means known currently or by other methods which are likely to be devised in the future. One such alternative light field sensor may use an array of pinholes instead of a lenticular array. Another alternative may place the sensor array at a distance significantly different from the back focal plane of the lenticular array (Lumsdaine et al. "The Focused Plenoptic Camera", ICCP April 2009). Such variations may achieve advantages in terms angular or spatial resolution given a particular sensor or lenticular array spacing. Ren Ng describes properties of generalized light field sensors in his dissertation work which extend beyond the format of the simple lenticular array placed in front of a sensor array. It is to be understood that all such representations are included if we speak of a lens array as one such representation of a light field sensor.

The light field sensor concept has been exploited by Ren Ng, and others to create cameras which can digitally focus an image after it has been acquired. In a camera demonstrated by Ng et al, a 16 megapixel array was placed at approximately the rear focal plane of a 90,000 microlens array, such that each microlens should cover a sensor area of about 13×13 pixels. This light field sensor was then placed such that the microlens array was located at the back focal plane of a traditional camera such that the scene was approximately focused on the lens array. The resolution of reconstructed images was then 300 by 300 pixels. This example highlights the cost of the light field sensor—the resolution of the reconstructed image is much less than the number of pixels required in the sensor. However as pointed out in Ren Ng's thesis, the technological capacity to create image sensors with high resolution far exceeds traditional imaging demands. Canon announced in 2010 an image sensor with 120 megapixels for use in an SLR type camera. With consumer level commercialization efforts underway for light field cameras it is reasonable to assume that image sensor technology will evolve to meet demand for megapixel resolutions. A similar camera described by Lumsdain and Georgiev demonstrates how adjustments to the light field sensor geometry may be used to optimize resolution vs. depth of field. Raskar et al describe the problem of glare in photography in terms of light fields and demonstrate how glare behaves in ray space as a high frequency noise that can be reduced by outlier rejection (see for example Raskar et al. "Glare Aware Photography: 4D Ray sampling for reducing glare effects of camera lenses" Mitsubishi Electric Research Laboratories 2008 and U.S. Pat. No. 7,780,364).

Traditionally imaging of the retina has been performed by a fundus camera as recently reviewed by DeHoog et al. (DeHoog et al., "Fundus camera systems: a comparative analysis," Appl. Opt. 48, 221-228 (2009)). A schematic for a typical fundus camera is shown in FIG. 2. Light from illumination source 12 is directed along an illumination path 201 containing a series of lenses 11, 9, 7 and apertures 10,8, before being directed to the eye 1 of a patient using an annular minor 3 and objective lens 2. Light reflected from the eye 1 passes through the center of the annular minor 3 and into a collection arm where it is imaged at image plane 6 after passing through focusing lens 4 and photographic lens 5. The primary challenge in fundus imaging compared with other types of imaging is a large amount of unwanted light coming from structures other than the intended target of examination. Primarily this is the result of glare specularly reflected and scattered from surfaces in the imaging path. This is traditionally managed by careful design of the illumination and collection paths, including complex apertures at precisely aligned positions. Crossed polarization between illumination and collection systems has also been used to suppress corneal glare (see for example U.S. Pat. No. 4,998,818).

An additional challenge of fundus photography is that the operator or control system of the device must precisely align the camera to the patient's pupil each time a photograph is taken to avoid introducing glare artifacts to the image originating from light reflected and scattered from the cornea and iris of the eye. The need to precisely locate the camera to the eye has led to further complications in the design of the fundus camera. The most intuitive means to align the optical axis of a device to the pupil of the eye is to image the pupil directly along that optical axis and provide that image to the operator or control system. Because the fundus imaging path is typically designed to block any light scattered from the iris, and any optical element present in both the illumination path and the imaging path is a potential light scattering risk, Tawada describes a fundus camera which includes a separate imaging path for imaging the iris. This imaging path is removably coupled to the optical axis by a flip in mirror to avoid introducing artifacts to the fundus image during actual fundus imaging. Such a solution adds optical and mechanical complexity to a system design, resulting in additional design constraints, increased cost, and reliability risk. It is therefore an object of the present invention to apply a new sensor to fundus photography to overcome the above described limitations in the prior art.

SUMMARY

The inventors have found that the previously described "light field camera" may be applied to fundus photography. According to the invention, known benefits of the light field camera are maintained—notably aberration correction and digital focus correction. Novel features are also realized including dynamic optimization of collection pupil diameter, digital glare reduction, integrated and simultaneous pupil camera on the same image path and sensor as retinal image.

The purpose of this invention is to image the back portion of the eye at high resolution to derive medically relevant information which may be used to improve, restore or save a patient's visual function, or document the status of the tissue for non vision related problems, for example cancer. The device may be used to monitor the health of the retina and nearby structures. A similar device may be used to recover biometric identification information for security purposes. Related applications may be found in other applications where it is required to image through a small aperture, particularly where the illumination of the target must also be directed through the aperture, and accidental capture of illumination scattered from the aperture may corrupt the image. Examples of this may include back scattering microscopy, endoscopy, and industrial inspection of containers through a viewport.

The present invention has the following aims and advantages
  Provide high resolution imaging of the tissue near the retinal plane independent of depth of focus
  Provide clinically useful imaging of planes far from the retinal plane from the same acquisition.
  Provide significant reduction to the optical and mechanical complexity of a device to image the back of the eye
  Compensate for optical aberrations of the camera
  Compensate for optical aberrations of the eye
  Eliminate glare originating within the camera from the posterior image
  Eliminate glare originating within the corneal surface back-reflection from the posterior image
  Eliminate glare originating from illumination of the iris
  Relieve the operator or control system of the eye imaging device of the necessity to precisely control focus on the retinal plane
  Relieve the operator or control system of the eye imaging device of the necessity to precisely control the alignment pupil of the eye
  Record stereographic photography with a single exposure
  Eliminate expensive component in the traditional fundus camera including the annulus mirror and the ring stop assembly in the illumination path
  Simultaneously acquire data which can be used to provide a live image of the iris which may used for alignment to the pupil using the same optical path and sensor as used for retinal imaging.
  Improve the light collection efficiency of system by digital optimization of collection aperture.
  Generate images of one or more layers within the retinal thickness with a single acquisition.

DETAILED DESCRIPTION

The application of the light field sensor to fundus photography described herein highlights a number of advantages that may be generalized to any imaging system that must image an object by aligning to an external aperture, particularly if the illumination for the scene must also be directed through the aperture. One now has the freedom to place virtual spatial filters which may attenuate rays which contribute artifacts to the image with much finer and dynamic control than could be achieved with traditional mechanical stops. This allows the image to be constructed using more useful rays, less rays causing artifacts, and a less rigid design of the instrument and alignment to the aperture.

Figure 1:
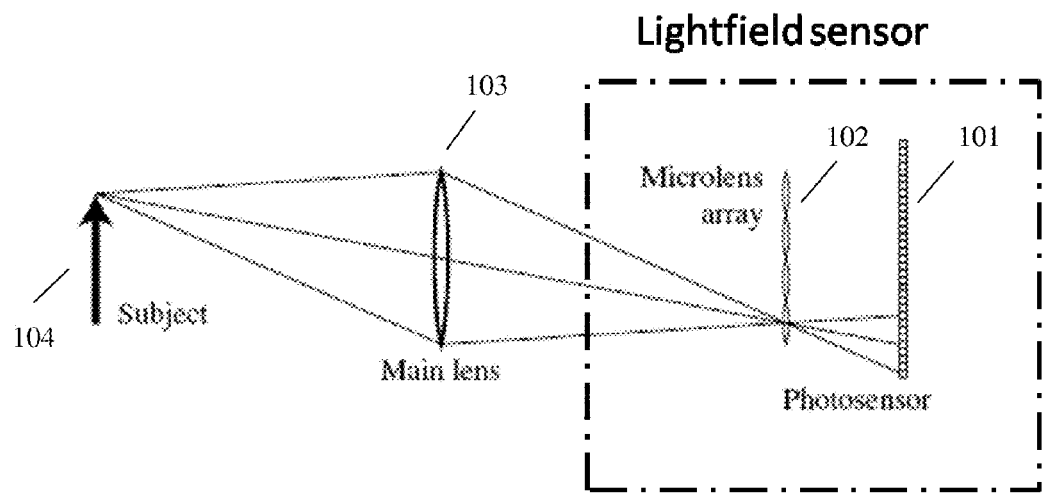
FIG. 1 illustrates the general concept of a light field sensor as is known from prior art.
Figure 2:
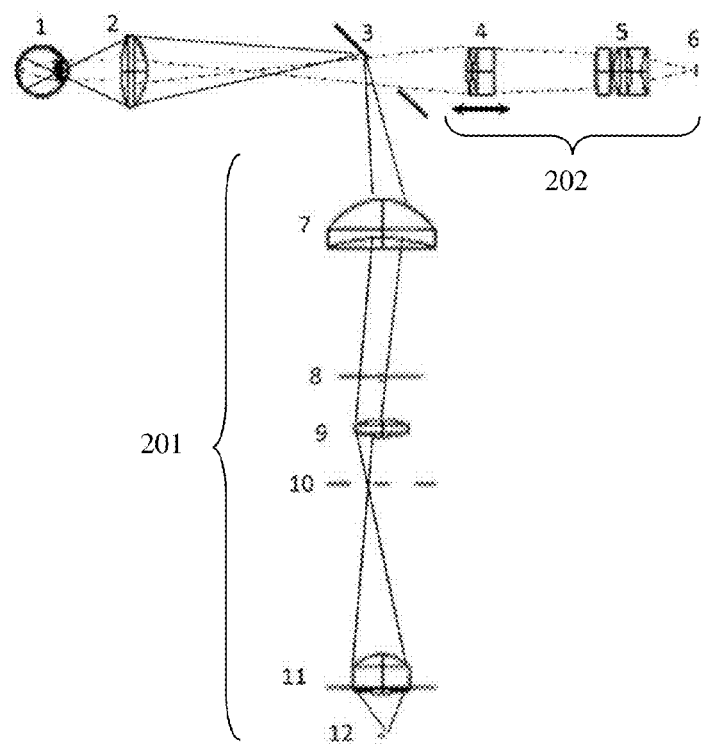
FIG. 2 illustrates a generalized fundus camera optical design as is known from prior art.
Figure 3:
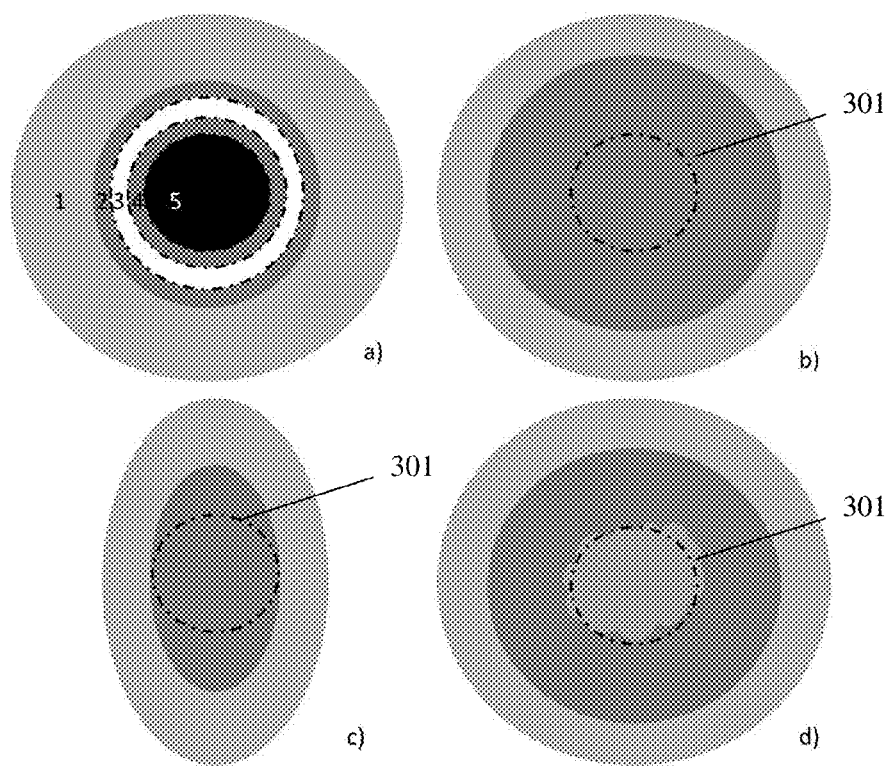
FIG. 3a illustrates the zones of the aperture of the eye relevant to fundus imaging.
FIGS. 3b, 3c, and 3d show examples of how dynamic changes and variations in pupil anatomy can limit the information available to a fundus imaging system.

The glare present in a fundus image if no glare reductions measures are taken is created by a fraction of the ray paths from the retina object to the retina image. In the traditional fundus camera design, an effort is made to place physical stops to block any ray path which contributes to glare (as shown in FIG. 2). At significant cost, modern designs are highly successful at blocking unwanted light coming from surfaces within the camera, and largely successful at blocking light reflecting from the cornea or scattered from the iris of the eye, if the eye is aligned within tight tolerances. In addition to eliminating the glare producing rays, such a restrictive design tends to occlude some rays which may otherwise contribute beneficially to the image. FIG. 3a displays an eye divided into five different zones. Zone 1 refers to the iris, zone 3 represents the illumination ring, and zone 5 is the collection zone of a typical fundus camera system limited by system apertures. Zones 2 and 4 are "dead zones", from which data is typically not collected, but possibly containing useful information. Another disadvantage of fixed apertures or pupil stops is that they cannot respond to changing eye conditions or pathological differences. FIG. 3b illustrates the case of a dilated pupil. Here if the pupil stop was limited to the size of zone 5 in FIG. 3a (indicated by dashed line 301), significant portions of the pupil would not be used for light collection. The same holds true in FIGS. 3c and 3d showing an elongated pupil or a cataract respectively.

Figure 4:
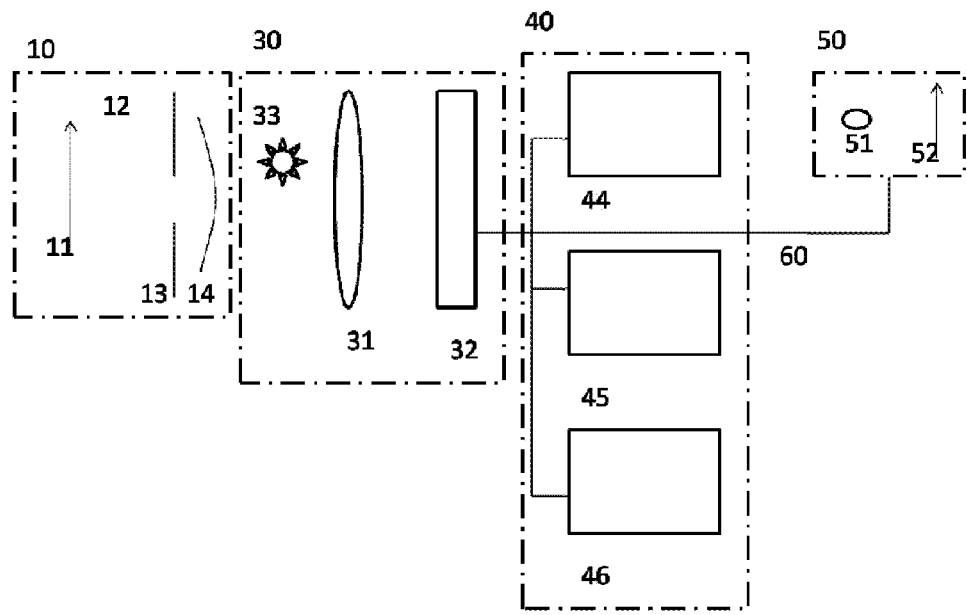
FIG. 4 shows the key components of an embodiment of a light field imaging system according to the present invention.

An embodiment of the present invention to image an object using a light field sensor through an external aperture is shown in FIG. 4. The main components of the system are an object of interest to image 10, an optical system 30, a data management unit 40, and display 50 to interface to the operator of the device. The object of interest 10 is generally separate from the optical system 30 and one of the two must in general be moved such that light may transfer from the area of interest to the light field sensor 32. The object to be imaged 10 may contain a particular feature which is desirable to observe at the highest imaging resolution represented in FIG. 4 as arrow 11. It may contain a substantially transparent intermediate media 12, an aperture that limits the signal and creates glare 13, and a specularly reflecting surface 14. The primary features which distinguish this imaging system over prior camera implementations of the light field sensor are related to dealing with difficulties arising from the object aperture in or near the pupil plane of the imaging system, and specularly reflecting surfaces 14, which create glare. The pupil plane of the imaging system may be defined by a plane conjugate to a traditional physical stop as described in a preferred embodiment below, or may be implemented as a feature of the lightfield sensor system. The optical system includes lens 31, a light field sensor 32, and an illumination system 33. The illumination system 33 has been shown as a part of the optical system 30, however it may be possible that the illumination system is part of the object 10, the imaging system 30 or independent from either, as in the case of ambient lighting. The primary optical system 30 serves to transport light from the object towards the lightfield sensor 32. In general, it converts the shape factor of the light from the object to the shape factor required by the light field sensor. For example the magnification of the system matches the field of view of the system to the light field sensor size. Further, the primary optical system may impose limits on the light as required by the lightfield sensor. For example, many implementations of light field sensors may require that the aperture stop be externally limited such that light from adjacent lenslets does not overlap on the sensor array. The data management system 40 performs all functions required to capture and process light field data into useful output, including creation of any views necessary for alignment, and reconstruction of planes within the object for final analysis, and storage of the data. The data management system shown in FIG. 4 includes a light field rendering engine 44 for data processing and reconstruction, a system memory 45, and a data storage unit 46. The data management system may be localized to the device or its functions may be distributed to a network. Such a network may include nodes which perform portions of this task which are quite general and are not dedicated to this device. A data bus 60 is shown to transfer information between the imaging system 30, the data management system 40, and the display unit 50. The display functions to inform the operator about the alignment status of the device, presents auxiliary information required for capturing the data, or related to the subject and may also present finished results from the image reconstruction.

Figure 5:
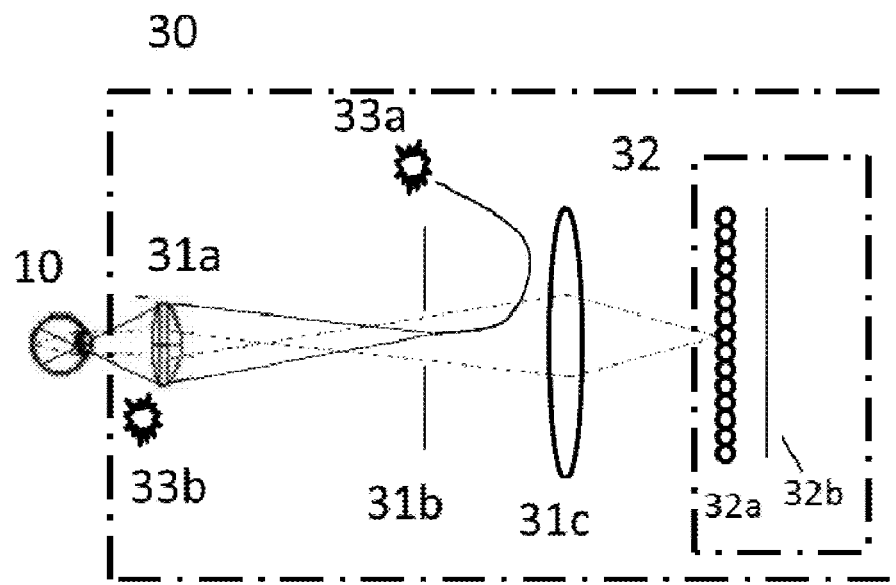
FIG. 5 shows a preferred embodiment of the optical subsystem of a light field fundus imaging system according to the present invention.

The optical subsystem 30 of a preferred embodiment of the present invention is shown in FIG. 5. Here the object of interest is the human eye 10. The retina of the human eye 10, which is a complex network of sensory, neural, and vascular components provides the target which should be imaged at high resolution. The non-pathological vitreous, lens and aqueous humor provide a substantially transparent media through which to image. The iris (and pathological components of the eye which should be transparent but are not) provide an aperture which may limit signal and create glare. The cornea is the optical surface with the most significant change in optical index of refraction, and therefore is most reflective, and most capable of creating reflected glare. The primary optical system 30 comprises an objective lens 31a which images the plane of the iris to a plane containing a pupil stop 31b which defines the field of view at the iris, and ultimately limits the alignment tolerance to the pupil. The pupil stop 31b provides the external aperture stop that is responsible for preventing light from adjacent lenslets in the light field sensor from overlapping in the sensor plane. It is desirable that this pupil stop has a shape that matches the pattern of the lenslet array. Thus, if the lenslet array 32a is in a Cartesian pattern (rows and columns), the pupil stop 31b should be square or rectangular. On the other hand, if the lenslet array 32a is hexagonal pattern, then the stop should be a hexagon, or possibly a circle as a circle as an approximation to a hexagon. The portion of the illumination system 33a for illuminating the retina is provided by a fiber tip at approximately the plane of the pupil stop 31b at a transverse location near the center of the field. This point should be approximately conjugate to a location within the patient's pupil. A fiber is used only because a source of limited spatial extent should be placed near the center of the aperture stop. Similarly a small light emitting diode, or larger source might be coupled in with the appropriate optics. The portion of the illumination system for illuminating the iris 33b may simply be ambient lighting or a low power light emitting diode placed surrounding the objective lens. The reimaging lens 31c placed between the pupil stop 31b and the light field sensor 32 reimages the retinal image to the lenslet plane 32a of the light field sensor. The existence, placement, and characteristics of this lens relative to the lightfield sensor is largely dependent on the degree to which lightfield spatial resolution is optimized to the retina, or pupil planes, as well as any standardization requirements that may be imposed by the light field sensor elements and the reconstruction algorithms. In a preferred embodiment the light field sensor 32 is constructed as a rectangular grid lenslet array 32a with a high resolution sensor 32b placed at the back focal plane of the lenslet array, but any type of light field sensor could be used in the present invention as would be recognized by one skilled in the art.

Figure 6:
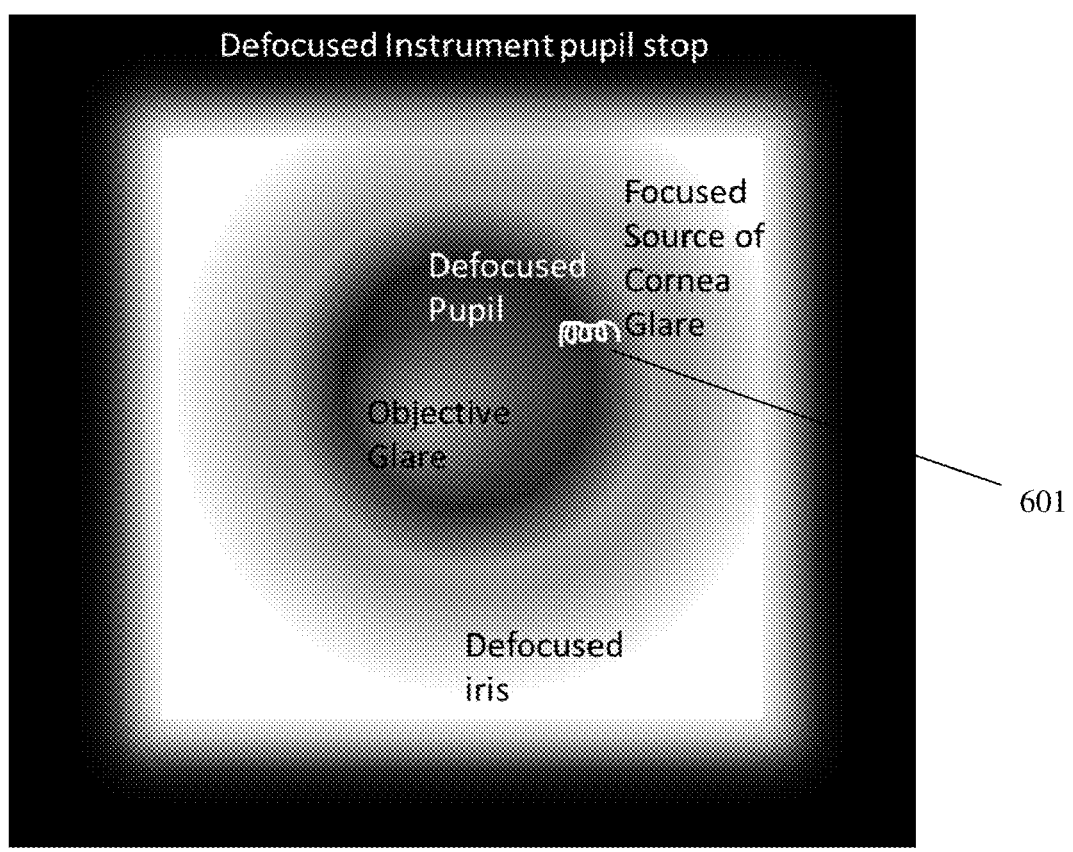
FIG. 6 shows a single plane of the light field of a human eye in which the source of cornea glare is in focus.

The sources of glare in a fundus photograph are well known. A first form of glare comes from light specularly reflected from the objective lens and cornea. A second and more persistently difficult form of glare comes from light scattered from the iris. A third form of glare originates with pathological media in the anterior eye. Each of these sources of glare can be described in terms of an image at a particular plane. For specularly reflected glare, a plane containing an image of the source can be calculated using standard lightfield processing techniques. An illustration of such a plane is shown in FIG. 6. The image shows a focused source of cornea glare, squiggle 601, as well as defocused images of the pupil, objective glare, and iris framed by the pupil stop. This plane contains a spatially compact set of rays that make up the cornea glare that may be identified and attenuated or rejected during the processing of the final image. As glare may be present from multiple reflecting surfaces, or from multiple illuminator sources existing at different planes, this process may be repeated at multiple locations throughout the collected lightfield and used to create a glare mask, which in the simplest form could set the intensity values of the glare contributing pixels to zero, so they will not influence the processing of the final image. As the imaging geometry is largely similar from instance to instance in the application of fundus photography, the expected location of the image of the illumination source may be used as a guide to optimize the processing time for subsequent acquisitions. Alternatively, one may choose to use statistical methods describing glare as described by Raskar et al. to deal with specularly reflected glare (Raskar et al. "Glare Aware Photography: 4D Ray sampling for reducing glare effects of camera lenses" Mistubishi Electric Research Laboratories 2008).

The source of the glare from the iris can be clearly imaged at the plane of the iris, which in the preferred embodiment is imaged quite close to the sensor array. In this plane it is advantageous to segment the pupil-iris boundary. Inside the pupil are contained the rays though which useful fundus information may pass. Outside the boundary lie rays which contribute to iris glare. It may be desirable to apply a weighting function to borderline pixels which may contain both useful and glare rays.

Figure 7:
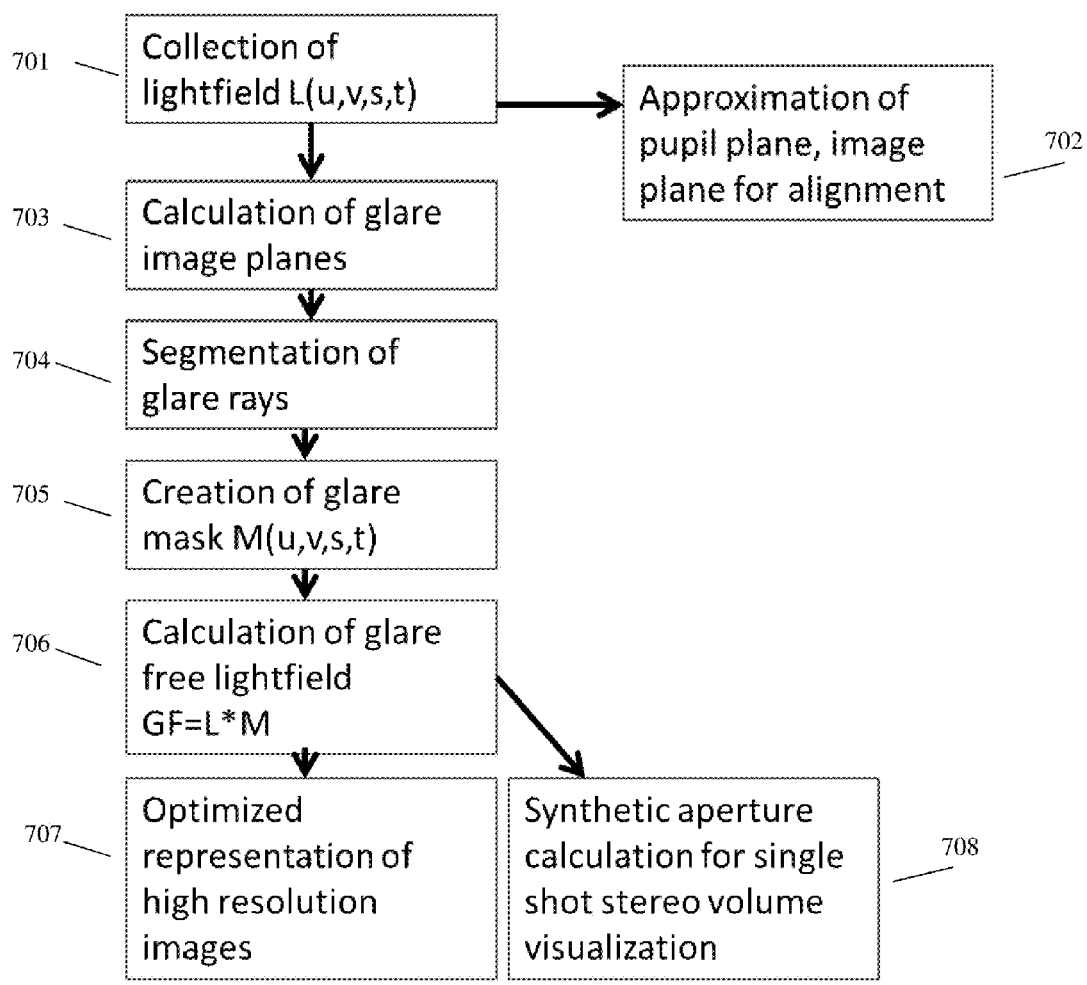
FIG. 7 illustrates the steps involved with an embodiment of the present invention in which sources of glare are removed from a light field image.

The third form of glare from opacities of a pathological anterior segment media are the most variable. In this case portions of the cornea or lens behind the pupil may not be suitable for transmitting information carrying light. Again in this case, the plane containing the offending structure may be rendered so as to achieve the most spatially compact representation of the artifact, undergo segmentation, and beam paths which correspond to the affected area may be attenuated. FIG. 7 describes a data flow for the optimization of images and reduction of glare according to the present invention. In summary, after the lightfield is collected using a light field sensor and optical imaging system (step 701), any number of glare image planes can be calculated (step 703) and segmented (step 704), to create a glare mask (705) to remove or reduce the effect of pixels containing signal originating for elements creating glare while calculating (step 706) and displaying an image (step 707) of the tissue under investigation.

The location of the plane(s) containing glare can typically be estimated by geometrical optics given a nominal alignment. In the preferred embodiment an illuminator is nominally imaged to the plane of the iris. The typical radius of curvature of a human cornea is 7.8 mm and the anterior chamber depth is 3 mm. The cornea therefore acts like a mirror with a focal length of $-r/2=-3.9$ mm. The action of this mirror is quite simply described using a form of the Gaussian lens equation:

$$\frac{1}{\text{object } dist} + \frac{1}{f} = \frac{1}{\text{image } dist},$$

allowing prediction of the location of the image of the reflection relative to the cornea. $1/3 \text{ mm} + 1/-3.9 \text{ mm} = 1/13 \text{ mm}$. The image of the reflected illuminator lies 13 mm behind the cornea (toward the retina). The above calculation approximates where the image of the illuminator reflected off the cornea appears to be in the space outside the eye.

For the current application it is more relevant to describe where the image of the illuminator reflected off the cornea appears to be in the space of the light field sensor. To do this precisely would require a first order specification of the complete optical system and would generally be best performed by ray tracing simulation of a given optical system. Because the lens array of the light field sensor is conjugate to the retina, we can provide a more general description by describing the position of the image of the illuminator reflected off the cornea as it appears to be in the space of the retina. For the following description of the plane of the glare to be valid, the image reconstruction parameters must be provided in units relevant to the retina space. If the optical power of the eye is approximated to be contained completely in the corneal surface, and the eye has length (and a focal length) of 20 mm we can perform a similar Gaussian lens calculation to find the image location in the retinal space. $1/13 \text{ mm} + 1/20 \text{ mm} = 1/8 \text{ mm}$. The image of the illuminator reflected off the cornea is imaged to a plane 8 mm behind the cornea (towards the retina) in the retinal space. This places the image 5 mm beyond the pupil with a remaining 12 mm away from the image plane. The above calculations illustrate how a plane might be estimated to first order, however in practice computer simulation, or simple experimentation will provide a much more accurate estimation of the location of the image of any particular illuminator in the light field sensor space. Once the planes containing glare are calculated, an optimized lightfield can be generated by attenuating or removing rays corresponding to positions of high light concentration and reconstructing an image from the remaining rays.

Figure 8:
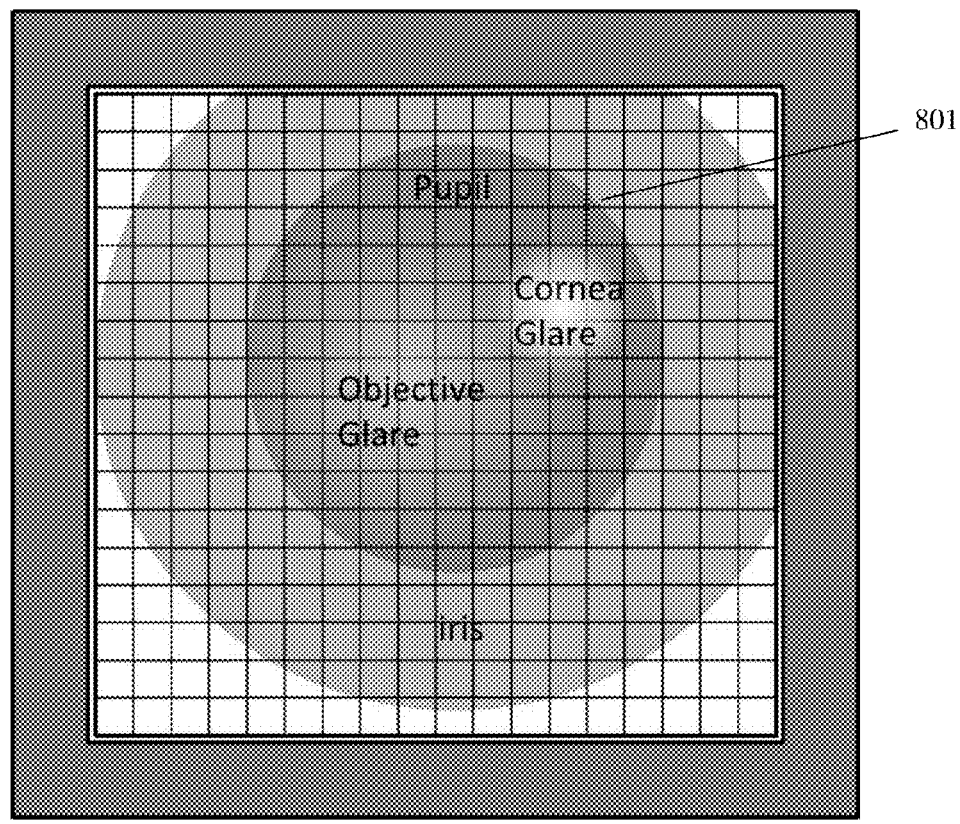
FIG. 8 shows an image of an eye that could be presented at the pixels under a single lenslet of a light field sensor.

Additionally the information in the light field can be used to align the camera to the patient and pupil without introducing a separate light path and sensor. FIG. 8 shows the image resulting on a collection of pixels underneath a single lenslet in the lens array of the light field sensor when the eye is nominally aligned to the instrument. Grid lines indicate individual sensor pixels and the frame around the image corresponds to the pupil stop, preventing light rays traveling through the lenslet from being imaged on adjacent pixels. Notably, the distribution of pixels underneath each lenslet in the light field sensor is an image of the pupil of the instrument in a preferred embodiment of the invention, and when aligned properly, is approximately the pupil of the patient's eye 801. The pupil image may be reconstructed from a simple averaging of the field under all, or a subset of the lenslets and used to provide information to the user on the display in an alignment mode related to the positioning of the patient relative to the instrument (step 702 of FIG. 7). The extent to which the image information changes underneath to the different lenslets also gives information about the axial alignment. If a simple averaging of pupil images under multiple lenslets is presented, the best axial alignment is recognized as the image with the least blurring effect. Mathematical correlation of pupil images may provide quantitative alignment feedback such as may be desirable to automatically position an instrument.

The use of light field cameras in fundus photography makes it possible to generate images of multiple tissue layers from a single acquisition. In the simplest case, this could be accomplished by selecting different focus depths in the tissue to generate multiple images. A more complex solution might be to follow a tissue layer such as the retinal pigment epithelium (RPE), processing the data so as to adjust the focus depth as a function of transverse location on the tissue so as to maintain the focus on the tissue layer of interest. For a layer that is harder to distinguish, like the cones, one could use an offset from a more easily found boundary like the RPE to follow the layer of interest.

The reconstruction of image planes from lightfield data is known to be computationally expensive (although computational hardware optimized towards this purpose is already widely available). Although the light field contains information about many possible reconstructed planes, it is generally impractical to reconstruct all of these planes simultaneously. For any required plane that is near a known position, it may be advantageous to calculate an approximate image based on the a priori information, or it may be preferable to calculate a more exact representation of the image at that plane. Additionally, approximations may be extremely useful for live data acquisition and alignment functions, while more calculation intensive operations may be used for offline post-processing. For example, during alignment, the exact position in space of the image of the reflected illumination may be constantly changing, but is always located near a particular known location. In such a case it may be possible to approximate the blocking of glare such that most of the glare is eliminated, while possibly allowing a little more glare, or a few less useful rays than ideal for the sake of expediency during data acquisition. Additionally it is not required that the alignment image of the retina have the full detail and signal to noise ratio required from the final processed image—it is only required to see certain large fiducials that can be determined with low lateral resolution. In such a case it may be advantageous to calculate an approximate image using a subset of data or using a fixed routine that may be implemented most easily in ultrafast computation hardware. In any case the full lightfield is recorded and may be processed in full detail in a post-processing stage.

Synthetic aperture processing of data may limit the aperture used to render a particular image to a smaller set of rays than is actually available from the full segmented pupil (step 708 of FIG. 7). This may be used to several useful effects in fundus imaging. First a lower resolution image of the fundus can be generated without a need to precisely determine the correct plane of focus for alignment purposes. Second, images using a smaller subset of the data may be calculated using less computation, and are particularly suited to alignment or other exploratory processes. Third, if the aberrations of the eye are significant, it may be desirable to limit the collection aperture of the optical system to reject the most aberrated light, and thus improve the image quality. Finally, stereo pairs can be generated from a single acquisition. (Note that it is traditionally required to take a pair of images that use a partially overlapping pupil). Techniques for synthetic aperture processing are described in detail in the thesis by Ren Ng, hereby incorporated by reference.

Techniques for correction for optical aberrations may be performed as described by Ren Ng's thesis. This may be applied as previously described by remapping of the collected lightfield, to a corrected light field from which to generate the image, to correct for aberrations introduced by the instrument, which are generally defined by the design of the instrument and do not change significantly with time. It may also be applied to the aberrations introduced by the object of interest. In the case of the human eye, these aberrations may be irregular across the field of view, may change with time as the tear film evolves on the corneal surface, as well as being significantly different from individual to individual. In the application of medical endoscopy it is common that the window of the instrument may be contaminated by more or less transparent fluids such as lubricants or mucous. In this case aberration as well as glare may dynamically change as the instrument is being used. In these cases aberration correction may correct for any combination of the fixed instrument aberrations, typical aberrations of the object, or optimized aberrations determined from examination of the specific object or collected dataset. For small aberrations as typically encountered in retinal imaging these various contributions do approximately separate and can be dealt with independently.

Figure 9:
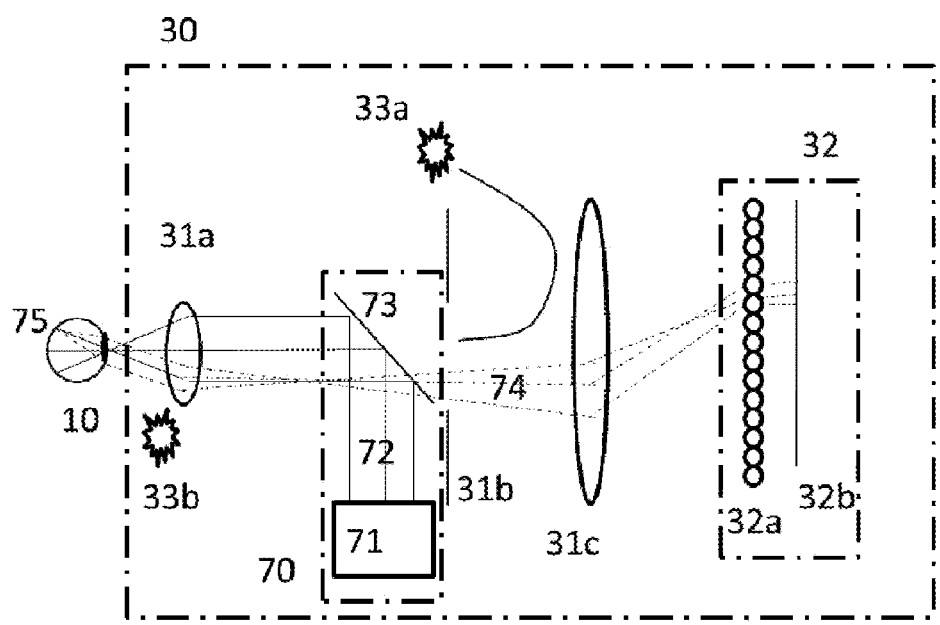
FIG. 9 shows an embodiment of the optical subsystem of a light field fundus imaging system according to the present invention, highlighting aspects of an aberrometer subsystem.

FIG. 9 illustrates how the optical system 30 may be modified by the addition of a wavefront illumination subsystem 70 for the unambiguous measurement of wavefront aberrations with this device. The wavefront illumination subsystem 70 consists of a light source 71 which creates a series of probe beams with low numerical aperture 72 which are coupled to the beam path by a beam splitter 73. The beam splitter introduces the low numerical aperture probe beams 72 and allows the returned illumination 74 to pass to the lightfield sensor 32. Each of the low numerical aperture probe beams 72, illuminates a small isolated area 75 of the retina of the human eye 10. From each isolated illuminated area 75 is emitted a bundle of rays 74 transmitted through different portions of the instrument pupil stop 31b. So long as the illuminating spots are placed on the retina with sufficient spacing that the aberration of the eye does not cause the ray paths associated with one illuminated spot to be ambiguous with the ray paths associated with another illuminated spot, the information contained in the sparse light field is analogous to the Shack Harman aberrometer.

The wavefront illumination subsystem 70, and the portion of the illumination system 33a for illuminating the retina for the purpose of creating a retina image are generally not illuminated at the same time. The beamsplitter 73 is potentially removable when a retina imaging mode is desired. Alternatively the beamsplitter may be practically invisible to the retina illumination 33a if the coating on the beamsplitter has minimal reflectivity for wavelengths used in the retina illumination source 33a, while maintaining partial reflectivity at the wavelength used for wavefront illumination source 71. If sufficient power is present in the wavefront illumination source 71, the reflectivity of the beamsplitter 73 can be low also at the wavelengths used for the wavefront illumination source 71, allowing efficient collection of the light which is incident on the eye. In any case, all wavelengths should be within the sensitivity band of the lightfield sensor 32. The light source 71 creates one or many small numerical aperture beams and may be realized by a scanning system, or parallel illumination.

The wavefront illumination system described in the previous paragraph can be used to describe the concept and an example of the mechanics of remapping a sensor field S(a,b,c,d) to an aberration free lightfield L(u,v,s,t). We define the sensor field S according to the preferred embodiment of the lightfield sensor, such that each array of pixels under a lenslet has coordinates (a,b), and within each array a pixel has coordinates (c,d). In an unaberrated case, each array of pixels under a lenslet (a,b) corresponds to a position in object space (u,v), while each pixel (c,d) corresponds to a position in the pupil which is straight forwardly related to the beam angles (s,t) in the lightfield. Starting from the point on the retina 75 from which rays return, all of this light nominally originated from a single point in space. This light will be measured on the lightfield sensor as $S(a_m, b_m, c_m, d_m)$. It shall be a goal of the remapping to make all of these rays converge at a single point in space in the corrected light field at the nominal focal plane, at the gold standard location specified by the input ray ($u_i, v_i$ coordinates). In the aberrated case, to the extent that the lightfield sensor is itself aberration free, each ray incident on the detector will be accurately mapped to a position in the instrument pupil by its pixel position under the lenslet (c,d)), but will be incident on the incorrect location in image space (i.e., a,b coordinates are not equal to u,v coordinates by which lenslet on which it is incident.) In fact, the rays will be distributed to many different lenslets in relation to the blur diameter of the imaged point. In each of the illuminated lenslets (corresponding a,b coordinates) the illuminated pixels (corresponding c,d coordinates) will indicate from which part of the pupil he illuminating rays originated. For each position within the pupil (corresponding c,d coordinates), it will be possible to define a ray error, which indicates the vector remapping of the measured coordinates (a,b) towards the corrected coordinates (u,v). The new coordinates of a corrected sensor field:

$$SC(u,v,c,d) = S(a+(u_i-a_m), b+(v_i-b_m), c, d)$$

In the case where the instrument pupil is the limiting aperture, there will be an illuminated pixel (c,d) corresponding to each portion of the instrument pupil. In the case that the object pupil limits the returning rays, some portions (c,d) of the instrument pupil should be eliminated from the above mapping (e.g. masking as described above). The aberrations are typically field dependent, so the aberrated field must be sampled at multiple locations 75, however the aberrations are assumed to vary slowly across the field such that the shift vector can be interpolated between measurements at discrete fields. To map to the light field $L(u,v,s,t)$ one must simply scale the (c,d) pupil coordinates to ray angles in object space.

The size of the data created by light field photography may be quite large compared to traditional photography. In the case where the aperture is severely limited by the object, as in fundus photography, and the alignment aperture is desired to be larger than the object aperture as described here—there exists a large part of the light field that is devoted to rays outside the useful aperture of the system. Because useful rays are determined by a relatively simple segmentation at the iris plane, it is possible to significantly reduce the file size by saving only data about these rays, and perhaps only the most summary data about the rays outside.

Although various applications and embodiments that incorporate the teachings of the present invention have been shown and described in detail herein, those skilled in the art can readily devise other varied embodiments that still incorporate these teachings. In particular, while the eye has been used as the preferred object of imaging, the techniques described herein could be applied to imaging of other objects especially those in which glare created by surfaces at other depth locations than the region of interest impacts the quality of an image of the region of interest.

THE FOLLOWING REFERENCES ARE HEREBY INCORPORATED BY REFERENCE

Patent Documents

U.S. Pat. No. 7,364,295 Tawada, Fundus Camera
U.S. Pat. No. 6,065,837 Goldfain et al. Ophthalmascope comprising defocused light source
U.S. Pat. No. 4,998,818 Kugler et al. Ophthalmascope with linear polarizer
U.S. Pat. No. 7,936,392 Yi-Ren Ng et al. "Imaging arrangements and methods therefore."
U.S. Pat. No. 7,780,364 Raskar et al. "Apparatus and method for reducing glare in images"

Non Patent Literature

Ren Ng "Digital light field photography" Doctoral Thesis 2006
Raskar et al. "Glare Aware Photography: 4D Ray sampling for reducing glare effects of camera lenses" Mistubishi Electric Research Laboratories 2008.
Ren Ng et al. "Light Field Photography with a handheld Plenoptic camera" Stanford tech report 2005.
Lumsdaine et al The Focused Plenoptic Camera, ICCP, April 2009.
Allan et al., "Holocamera for 3-D micrography of the alert human eye," Appl. Opt. 19, 2219-2225 (1980)
DeHoog et al., "Fundus camera systems: a comparative analysis," Appl. Opt. 48, 221-228 (2009) http://www.canon.com/news/2010/aug24e.html "Canon successfully develops world's first APS-H-size CMOS image sensor to realize record-high resolution of 120 megapixels"

What is claimed is:

1. An ophthalmic imaging system, said system comprising:
an illumination light source;
a detector for collecting both positional and directional information of the ray paths of illumination light reflected from the eye of a patient;
optics for directing the illumination light source to the eye of the patient and for directing light reflected from the eye of the patient to the detector;
a processor for processing the positional and directional information and for generating an image of the eye of the patient using the positional and directional information; and
a display for displaying the image.

2. A system as recited in claim 1, wherein the detector is a light field sensor consisting of a two dimensional sensor array behind a microlens array.

3. A system as recited in claim 2, wherein the distance between the microlens array and the sensor array is the focal length of the microlens array.

4. A system as recited in claim 2, wherein the microlens array of the light field sensor is located approximately conjugate to the retina of the eye.

5. A system as recited in claim 1, wherein the processor compensates for optical aberrations present in the imaging system.

6. A system as recited in claim 1, wherein the imaging system is used to image the posterior section of the eye and the iris of the eye acts as an aperture.

7. A system as recited in claim 6, wherein the processor generates a high resolution image of the retina of the eye of a patient.

8. A system as recited in claim 1, wherein the processor reduces unwanted intensity information associated with reflections and scattering from portions of the eye other than the fundus to reduce glare in the image.

9. A system as recited in claim 1, wherein the processor reduces intensity information associated with specular reflections from the cornea of the eye.

10. A system as recited in claim 1, wherein the processor reduces intensity information associated with light scattered from the iris.

11. A system as recited in claim 1, wherein the processor reduces intensity information associated with pathological media located in the anterior portion of the eye.

12. A system as recited in claim 1, wherein the processor generates two images of the eye, each at a different depth in the eye.

13. A system as recited in claim 1, wherein the processor calculates a synthetic aperture and applies the aperture to the signals to limit the image to a subset of light that is measured.

14. A system as recited in claim 1, wherein the processor generates an image of the pupil plane of the instrument to aid in alignment of the instrument.

15. A system as recited in claim 1, further comprising a light source that generates light of low numerical aperture for characterizing aberrations.

16. A method of obtaining images of the fundus of the eye of a patient comprising the steps of:
   illuminating the eye with a light source;
   capturing light rays reflected from the eye with a light field sensor, said sensor generating signals representative of both the position and direction of the captured light rays; and
   processing the signals to generate an image of the fundus of the eye.

17. A method of obtaining images as recited in claim 16, wherein said processing step operates to reduce unwanted intensity information associated with reflections and scattering from portions of the eye other than the fundus to reduce glare in the image.

18. A method of obtaining images as recited in claim 17, wherein said processing step determines position and direction values from which unwanted reflections or scattering are occurring in order to reduce the unwanted intensity information from the image.

19. A method of obtaining images as recited in claim 17, wherein the processing step reduces intensity information associated with specular reflections from the cornea of the eye.

20. A method of obtaining images as recited in claim 17, wherein the processing step reduces intensity information associated with light scattered from the iris.

21. A method of obtaining images as recited in claim 17, wherein the processing step reduces intensity information associated with pathological media located in the anterior portion of the eye.

22. A method of obtaining images as recited in claim 17, wherein the processing step functions to reduce aberrations in the image.

23. A method of obtaining images as recited in claim 17, wherein the processing step includes generating multiple images, each at a different depth in the retina.

24. A method of obtaining images as recited in claim 17, wherein the processing step calculates a synthetic aperture and applies the aperture to the signals to limit the image to a subset of light that is measured.

25. A method on obtaining images as recited in claim 24, wherein stereo images are generated.

* * * * *

UNITED STATES PATENT AND TRADEMARK OFFICE
CERTIFICATE OF CORRECTION

| | |
|---|---|
| PATENT NO. | : 8,998,411 B2 |
| APPLICATION NO. | : 13/542516 |
| DATED | : April 7, 2015 |
| INVENTOR(S) | : Alexandre R. Tumlinson et al. |

It is certified that error appears in the above-identified patent and that said Letters Patent is hereby corrected as shown below:

On Title page 2, in column 2, under "Other Publications", line 9, delete "Mistubishi" and insert -- Mitsubishi --, therefor.

In the Specification,

In column 1, line 59, delete "reference" and insert -- reference. --, therefor.

In column 2, line 38-39, delete "Lumsdain" and insert -- Lumsdaine --, therefor.

In column 2, line 46, delete "Mistubishi" and insert -- Mitsubishi --, therefor.

In column 2, line 55, delete "minor" and insert -- mirror --, therefor.

In column 2, line 57, delete "minor" and insert -- mirror --, therefor.

In column 7, line 25, delete "Mistubishi" and insert -- Mitsubishi --, therefor.

In column 11, line 62, delete "Ophthalmascope" and insert -- Ophthalmoscope --, therefor.

In column 11, line 64, delete "Ophthalmascope" and insert -- Ophthalmoscope --, therefor.

In column 12, line 9, delete "Mistubishi" and insert -- Mitsubishi --, therefor.

In the Claims,

In column 14, line 26, in claim 25, delete "on" and insert -- of --, therefor.

Signed and Sealed this
Eighteenth Day of August, 2015

Michelle K. Lee
*Director of the United States Patent and Trademark Office*